(12) United States Patent
Bergersen (10) Patent No.: US 7,716,062 B2
(45) Date of Patent: May 11, 2010

(54) DENTAL APPLIANCES AND SYSTEMS AND METHODS FOR DISTRIBUTING DENTAL APPLIANCES

(75) Inventor: Earl O. Bergersen, Dorado, PR (US)

(73) Assignee: Ortho-Tain Inc, Toa Alta, PR (US)

( * ) Notice: Subject to any disclaimer, the term of this patent is extended or adjusted under 35 U.S.C. 154(b) by 1182 days.

(21) Appl. No.: 10/447,098

(22) Filed: May 28, 2003

(65) Prior Publication Data

US 2003/0225594 A1 Dec. 4, 2003

Related U.S. Application Data

(60) Provisional application No. 60/383,909, filed on May 28, 2002.

(51) Int. Cl.
 *G06Q 10/00* (2006.01)
(52) U.S. Cl. ........................................... 705/1
(58) Field of Classification Search ....................... 705/1
 See application file for complete search history.

(56) References Cited

U.S. PATENT DOCUMENTS

| | | | |
|---|---|---|---|
| 5,209,660 A * | 5/1993 | Speckmann | 433/181 |
| 5,882,192 A | 3/1999 | Bergersen | 433/2 |
| 6,572,372 B1 * | 6/2003 | Phan et al. | 433/6 |
| 6,582,225 B1 | 6/2003 | Bergersen | 433/2 |
| 6,688,885 B1 * | 2/2004 | Sachdeva et al. | 433/24 |
| 2002/0188478 A1 * | 12/2002 | Breeland et al. | 705/3 |
| 2007/0292821 A1 * | 12/2007 | De Vreese | 433/195 |
| 2008/0160473 A1 * | 7/2008 | Li et al. | 433/3 |
| 2009/0194133 A1 * | 8/2009 | Toor | 132/324 |

FOREIGN PATENT DOCUMENTS

WO PCT/US03/16733 5/2003

* cited by examiner

*Primary Examiner*—Pierre E Elisca
(74) *Attorney, Agent, or Firm*—Patents +TMS P.C.

(57) ABSTRACT

Dental appliances and systems and methods for distributing dental appliances are provided. The dental appliances may be worn within a mouth of a patient to treat a dental condition. The dental appliances may be distributed to the patient through various venues. The venues range from those in which the patient has direct contact with a care provider to those in which the patient is able to independently determine an appropriate dental appliance to treat the dental condition. As a result, the amount of interaction between the patient and a care provider is significantly reduced, as well as an overall cost of treatment. The time necessary for appointments, if any, is also reduced and/or eliminated.

51 Claims, 10 Drawing Sheets

DENTAL APPLIANCES AND SYSTEMS AND METHODS FOR DISTRIBUTING DENTAL APPLIANCES

This application claims the benefit of U.S. Provisional Application Ser. No. 60/383,909, filed May 28, 2002.

BACKGROUND OF THE INVENTION

The present invention relates to dental appliances and systems and methods for distributing dental appliances. More specifically, the present invention relates to dental appliances which may be pre-formed and/or customized for an individual. The dental appliances may be distributed in various venues, such as, for example, care provider offices, department stores, pharmacies, or other venues.

It is generally known to provide dental care to a patient. Typically, the patient may visit, for example, a dentist or other type of care provider at the office of the care provider. The dentist, for example, may then examine the patient using various techniques, including x-raying the area to be treated and/or other impression-taking techniques, such as study models. The dentist may then provide the patient with a dental appliance to treat the condition of the patient. For example, a patient may have an overbite which may require a dental appliance to be placed within the mouth of the patient for an amount of time. The dentist treating the patient may take an impression of an interior of the mouth of the patient. The models may be used to determine a size or a shape of a dental appliance which may be worn by the patient to treat the overbite.

In some cases, a patient may require a number of subsequent visits to the office of a dentist to treat a dental condition. The subsequent visits may include adjustments or alterations of the appliance or other follow-up services that may be performed on the patient. The subsequent visits may also include additional dental appliances provided to the patient to address, for example, different stages of treatment of a dental condition. As a result, an overall cost of the dental care provided to the patient may increase substantially. Further, potential patients may be adverse to seeking dental care because of the substantial costs associated with dental services and/or dental appliances, as well as the time commitment necessary for the dental visits including, examination, diagnosis and follow-up care.

A need, therefore, exists for dental appliances and systems and methods of distributing dental appliances wherein an amount of interaction between the care provider and the patient is reduced or eliminated.

SUMMARY OF THE INVENTION

The present invention relates to dental appliances and systems and methods for distributing dental appliances. More specifically, the dental appliances may be worn within a mouth of a user to treat a dental condition without adjustments or appointments with a professional or other provider. The dental appliances may be shaped to receive individual teeth of the user, or may have a flat occlusal area, or may be a combination of both. The dental appliances may be pre-formed and/or customized. Moreover, one or more dental appliances may be used to treat various stages of a dental condition.

The dental appliances may be distributed in various venues. In one embodiment, the venue is an office of a care provider. In another embodiment, the venue is an orthodontic office operated in a manner of a franchise or chain located within a shopping center or mall, for example. In yet another embodiment, a machine may be used to examine a prospective patient and dispense a dental appliance to the patient. In another embodiment, the patient may be able to purchase one or more dental appliances in an over-the-counter manner.

To this end, in an embodiment of the present invention, a method is provided for distributing a preformed dental appliance to a patient wherein the pre-formed dental appliance is one of a plurality of types of preformed dental appliances wherein each type of pre-formed dental appliance corresponds to one of a plurality of types of orthodontic conditions. The method comprises the steps of: diagnosing the patient as having one of the types of orthodontic conditions; and providing the patient with the type of pre-formed dental appliance corresponding to the type of orthodontic condition.

In an embodiment, the method further has the step of wearing the pre-formed dental appliance to treat a malocclusion.

In an embodiment, the method further has the step of placing an advertisement for the dental appliances prior to the patient visiting the office.

In an embodiment, the dental appliance is delivered to the patient from a location remote from the office.

In an embodiment, the method further has the step of customizing the dental appliance prior to providing the dental appliance to the patient.

In another embodiment of the present invention, a method is provided for distributing a dental appliance to a patient through an office within a chain of offices providing dental care wherein the dental appliance is one of a plurality of types of dental appliances wherein each type of dental appliance corresponds to one of a plurality of types of orthodontic conditions. The method comprises the steps of: examining the patient; diagnosing the patient as having one of the types of orthodontic conditions; and providing the patient with the type of dental appliance corresponding to the type of orthodontic condition.

In an embodiment, the dental appliance is a pre-formed dental appliance.

In an embodiment, the dental appliance is a customized dental appliance.

In an embodiment, the patient is examined by a machine.

In an embodiment, the patient is examined by a care provider.

In an embodiment, the dental appliance is manufactured at a location remote from the office.

In an embodiment, the patient is examined at a location remote from the office.

In another embodiment of the present invention, a method is provided for distributing a dental appliance to a patient through an orthodontic center located within a shopping center wherein the dental appliance is one of a plurality of types of dental appliances wherein each type of dental appliance corresponds to one of a plurality of types of orthodontic conditions. The method comprises the steps of: examining the patient; diagnosing the patient as having one of the types of orthodontic conditions; and providing the patient with the type of dental appliance corresponding to the type of orthodontic condition.

In an embodiment, the method further has the step of customizing the dental appliance prior to providing the patient with the dental appliance.

In an embodiment, the dental appliance is pre-formed.

In an embodiment, the method further has the step of delivering the dental appliance to the orthodontic center prior to providing the dental appliance to the patient.

In an embodiment, the patient is examined by a machine.

In an embodiment, the method further has the step of treating a malocclusion with the dental appliance.

In an embodiment, the patient is diagnosed at a location remote from the orthodontic center.

In another embodiment of the present invention, a method is provided for distributing a dental appliance to a patient. The method comprises the steps of: placing a dental appliance dispensing apparatus in a venue of a common carrier wherein the dental appliance dispensing apparatus stores one or more types of dental appliances which correspond to one or more types of orthodontic conditions; diagnosing the patient as having one of the types of orthodontic conditions; and dispensing the dental appliance to the patient wherein the type of dental appliance corresponds to the type of orthodontic condition.

In an embodiment, the method further has the step of treating a malocclusion with the dental appliance.

In an embodiment, the method further has the step of obtaining an image of the patient via the dental appliance dispensing apparatus.

In an embodiment, the method further has the step of obtaining an impression of the patient via the dental appliance dispensing apparatus.

In another embodiment of the present invention, a system is provided for distributing a dental appliance to a patient. The system has a dental appliance dispensing apparatus wherein the dental appliance dispensing apparatus has an image capturing device for obtaining an image of an interior of a mouth of the patient. The system also has a plurality of types of dental appliances stored within the dental appliance dispensing apparatus wherein each type of the plurality of types of dental appliances correspond to a type of orthodontic condition. In addition, the system has a central processing unit located remote from the dental appliance dispensing apparatus wherein the central processing unit is connected to the dental appliance dispensing apparatus wherein the central processing unit diagnoses the image obtained of the mouth of the patient into one of the types of orthodontic conditions.

In an embodiment, two or more of the dental appliances correspond to consecutive stages of treatment of a malocclusion.

In another embodiment of the present invention, a method is provided for distributing a dental appliance to a patient wherein the dental appliance is one of a plurality of types of dental appliances wherein each type of dental appliance corresponds to one of a plurality of types of orthodontic conditions. The method comprises the steps of: providing an orthodontic kit wherein the orthodontic kit contains a wafer wherein the wafer obtains an impression of teeth; and diagnosing one of the orthodontic conditions based on the impression.

In an embodiment, the method further has the step of manufacturing the dental appliance at a location remote from where the impression of the wafer was obtained.

In an embodiment, the method further has the step of delivering one of the types of dental appliances to the patient based on the type of orthodontic condition diagnosed.

In an embodiment, the method further has the step of customizing the dental appliance prior to delivering the dental appliance.

In an embodiment, the dental appliance is pre-formed.

In an embodiment, the orthodontic kit contains information regarding at least one type of the orthodontic conditions.

In another embodiment of the present invention, a method is provided for distributing a dental appliance to a patient wherein the dental appliance is one of a plurality of dental appliances having a plurality of sizes. The method comprises the step of: providing each of the plurality of dental appliances in a package wherein the package contains information regarding a size of the dental appliance wherein the patient can select one of the plurality of sizes of dental appliances based on the information.

In an embodiment, the method further has the step of treating a malocclusion with the dental appliance.

In an embodiment, the package also contains information about a type of orthodontic condition.

In an embodiment, the information provides an actual size image of a tooth.

In an embodiment, each of the plurality of dental appliances corresponds to one of a plurality of types of orthodontic conditions.

It is, therefore, an advantage of the present invention to provide a dental appliance, or appliances, and systems and methods for distributing such appliances which reduce or eliminate the amount of interaction between a care provider and a patient.

Another advantage of the present invention is to provide dental appliances and systems and methods for distributing such appliances which lower an overall cost of dental care for a patient.

Yet another advantage of the present invention is to provide a dental appliance, or appliances, and systems and methods for distributing such appliances which provide a patient with increased accessibility to dental care.

Moreover, an advantage of the present invention is to provide a dental appliance, or appliances, and systems and methods for distributing such appliances wherein a single dental appliance may be used to treat a dental condition of a patient.

A further advantage of the present invention is to provide a dental appliance, or appliances, and systems and methods for distributing such appliances wherein the patient may be able to determine which dental appliance or appliances are appropriate for treating a dental condition of the patient.

Another advantage of the present invention is to provide a dental appliance, or appliances, and systems and methods for distributing such appliances which provides technical support to a patient after the patient receives a dental appliance.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to dental appliances and systems and methods for distributing dental appliances. The dental appliances may be worn within a mouth of a patient to treat a dental condition with minimum or no adjustments and/or appointments with a professional or other care provider. The dental appliances may be distributed to the patient through various venues. The venues range from those in which the patient has direct contact with a care provider to those in which the patient may independently determine an appropriate dental appliance to treat the dental condition without the need for a care provider.

Figure 1:
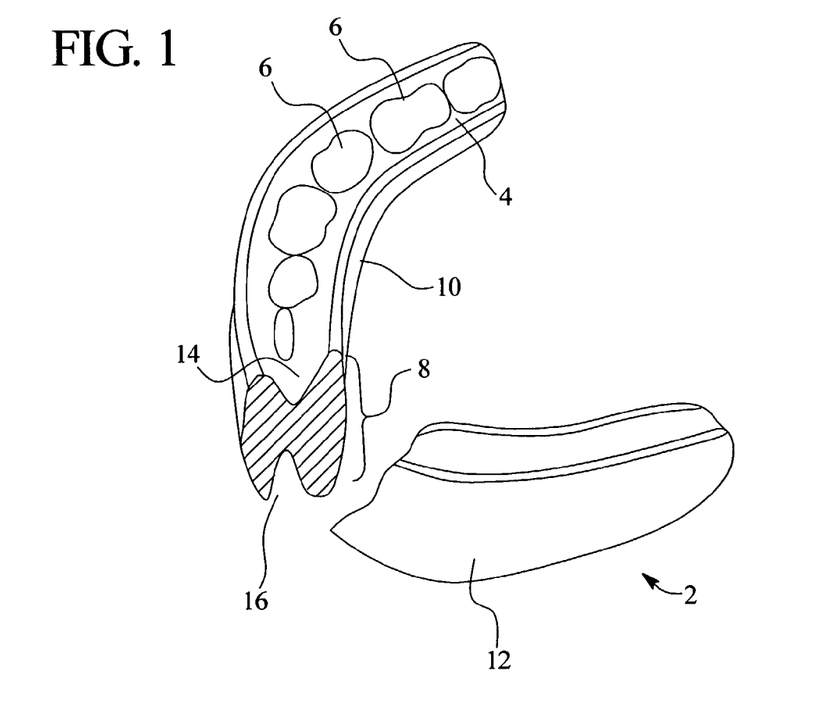
FIG. 1 illustrates a perspective view of a dental appliance in an embodiment of the present invention.

Referring now to the drawings, wherein like numerals refer to like parts, FIG. 1 illustrates a perspective view of a dental appliance 2 in an embodiment of the present invention. The dental appliance 2 may be constructed from, for example, plastic, rubber, polyvinyl chloride, acrylic, silicone, or the like. The dental appliance 2 may have an occlusal area 4 which may be contacted by one or more teeth of a user when the dental appliance 2 is placed within a mouth of the user. In addition, the occlusal area 4 may have individual sockets 6 for receiving individual, upper teeth and/or lower teeth of the user. A cross-section 8 is provided of an anterior segment of the dental appliance 2 wherein an area 14 for receiving an upper incisor and an area 16 for receiving a lower incisor may be seen in profile. The dental appliance may have a lingual shell 10 and an outer shell 12. The lingual shell 10 may be closer to the tongue of the user than the outer shell 12 when the dental appliance 2 is worn. The outer shell 12 may abut the cheeks of the user when the dental appliance 2 is worn.

The dental appliance 2 may be pre-fabricated and/or may be customized to fit within the mouth of the user. Moreover, one or more of the dental appliances 2 may be used within a program for treating a dental condition of the user. For example, the dental appliance 2 may be used to treat a dental condition such as, for example, overbite. The treatment may require two or more of the dental appliances 2. Each of the dental appliances 2 may be configured to treat a different stage of overbite.

Figure 2A:
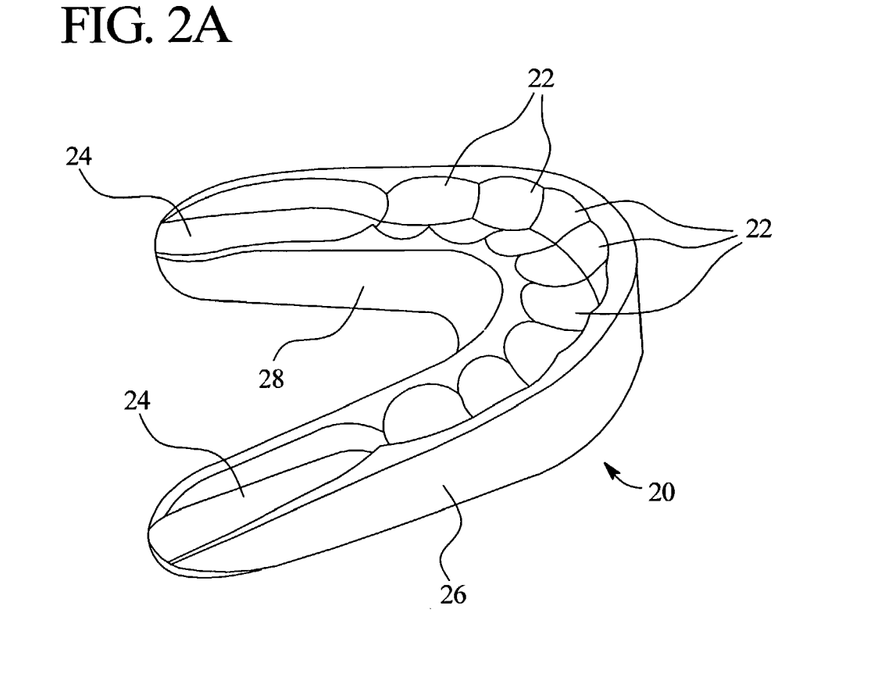
FIG. 2A illustrates a perspective view of a dental appliance in an embodiment of the present invention.

In another embodiment of the present invention, a dental appliance 20 is provided, as illustrated in FIG. 2A. The dental appliance 20 may be constructed from, for example, rubber, plastic, or the like. The dental appliance 20 may have sockets 22 for receiving individual upper teeth of the user. In addition, the dental appliance 20 may have flat areas 24 for receiving the teeth of an individual; specifically, a posterior second deciduous molar and a first permanent molar, or any combination of any number of teeth. The flat areas 24 may enable erupting teeth to be guided into place or slide forward or backwards along the flat areas 24.

The dental appliance 20 may also have an outer margin 26 which may provide a boundary for an outer side of the teeth of an individual. The outer side may be defined as a side of the teeth closest to the cheek, buccally, or to an exterior of the mouth of the user. The teeth of the user may contact the outer margin 26 when the dental appliance 20 is worn. A lingual margin 28 may provide a boundary for teeth located lingually or towards an inner side of the teeth of the user. The inner side may be defined by a side of the teeth furthest from the exterior of the mouth or cheeks.

Figure 2B:
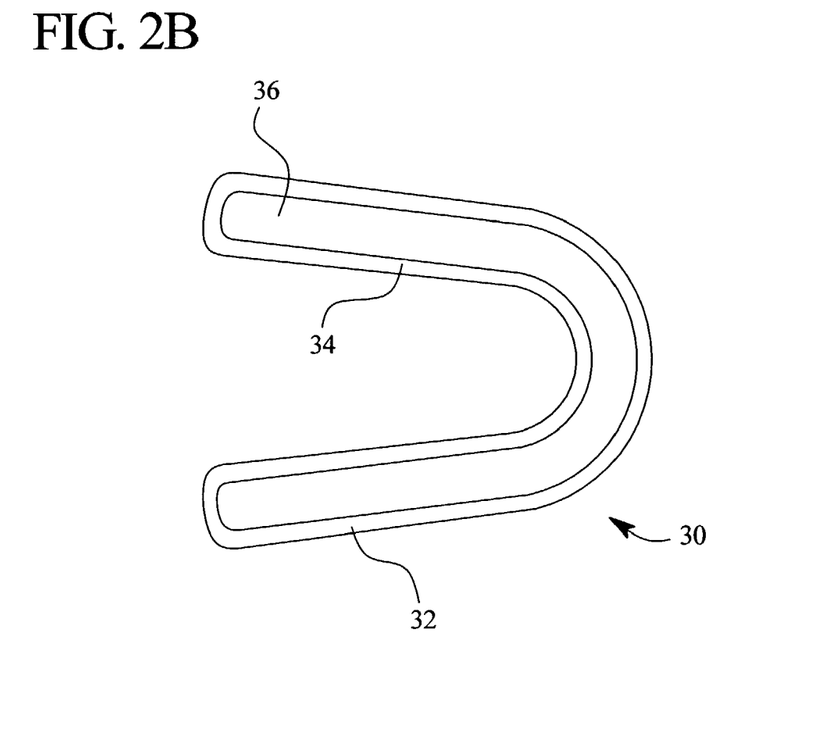
FIG. 2B illustrates a top plan view of a dental appliance in an embodiment of the present invention.

FIG. 2B illustrates a dental appliance 30 having an outer margin 32 and a lingual margin 34. The dental appliance 30 may also have a flat area 36 which extends along an occlusal surface of the entire dental appliance 30. The flat area 36 may receive each of the upper teeth of the user. In an embodiment, a bottom portion (not shown) of the dental appliance 30 may also have a flat area which may receive each of the lower teeth of the user. The bottom portion may be designed as a separate unit for the lower teeth and may be attached to an upper portion (not shown) for receiving teeth by, for example, snaps, hook-and-loop fasteners, or the like. In an embodiment, the bottom portion and the upper portion may be fixed together permanently. The dental appliances 20, 30 may be preformed or may be customized to fit within the mouth of a user. Moreover, one or more of the dental appliances 20, 30 may be used within different stages of treatment of a dental condition. The dental appliances 20, 30 may be designed to treat dental conditions of child, adolescent and/or adult patients.

Figure 3:
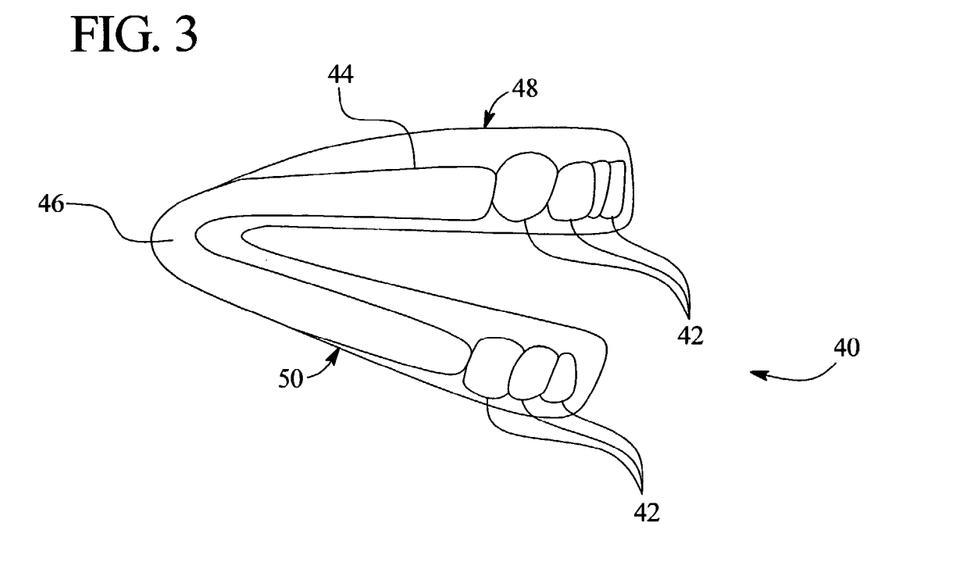
FIG. 3 illustrates a side view of a dental appliance in another embodiment of the present invention.

Referring now to FIG. 3, a dental appliance 40 is provided having sockets 42 for receiving individual upper teeth and lower teeth of the user. In other embodiments, the dental appliance 40 may have no sockets or sockets for each of the individual teeth of the user. Flat areas 44 may be provided for receiving the upper teeth and the lower teeth of the user; specifically, the first and second deciduous molars of the upper teeth and/or the lower teeth as indicated, or any combination of any number of deciduous and/or permanent teeth. In other embodiments, the flat areas 44 may extend for an entire occlusal area for the upper teeth and/or the lower teeth. In addition, the dental appliance 40 may have a hinged area 46 which may connect an upper portion 48 and a lower portion 50 of the dental appliance 40. The dental appliance 40 may be preformed and/or customized and may be used to treat the dental conditions of children, adolescents and/or adults.

Figure 4A:
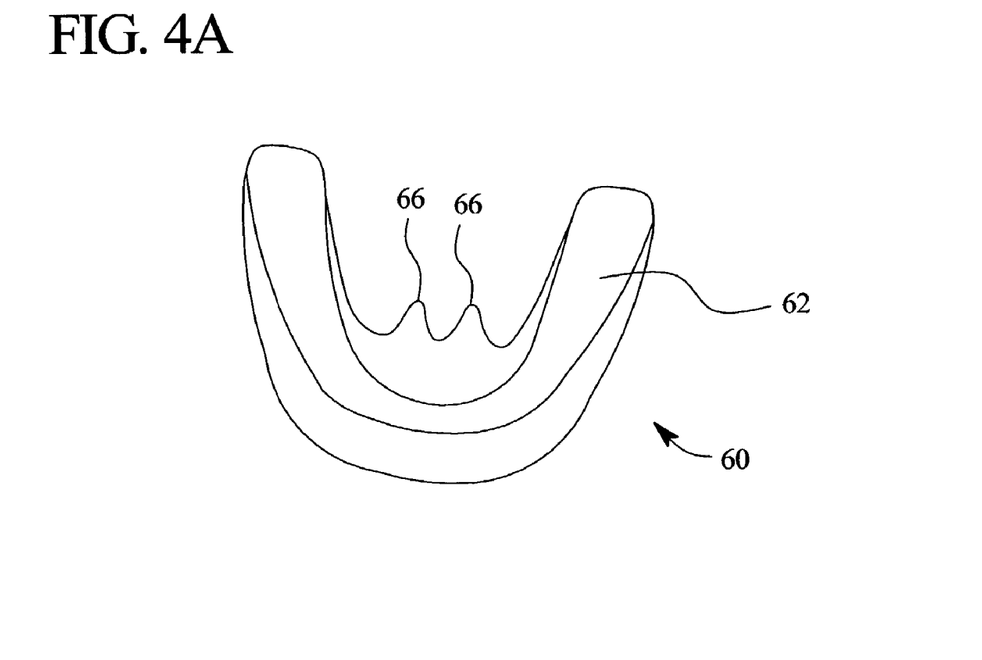
FIG. 4A illustrates a top plan view of a dental appliance in another embodiment of the present invention.
Figure 4B:
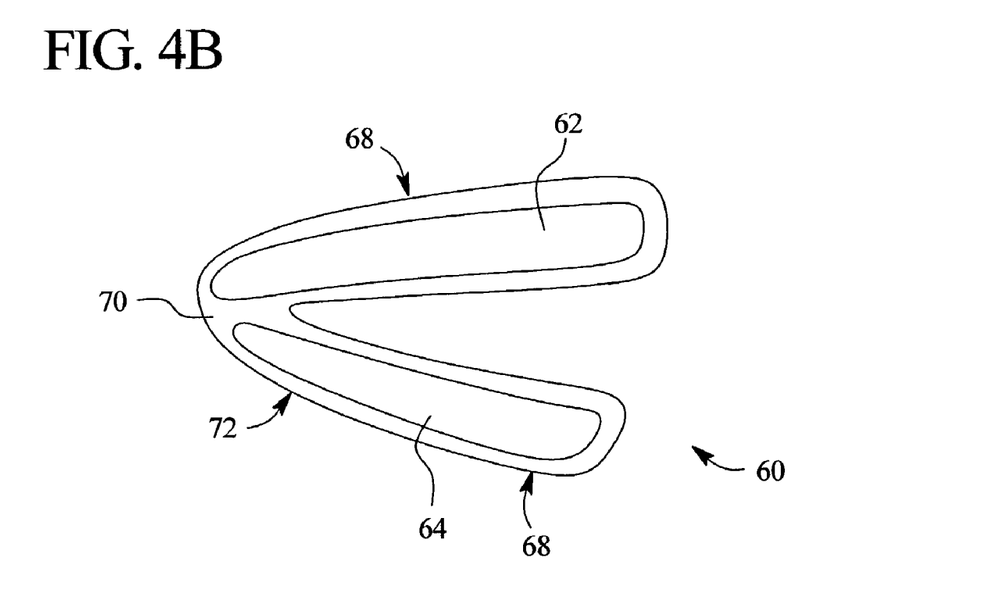
FIG. 4B illustrates a side view of a dental appliance in another embodiment of the present invention.

FIGS. 4A and 4B illustrate a dental appliance 60 having flat areas 62, 64 for receiving the upper teeth and/or the lower teeth, respectively. The dental appliance 60 may also have lingual tabs 66 extending from a lower portion 68 of the dental appliance 60. The lingual tabs 66 prevent a mandible of the user from slipping in a rearward direction from the lower portion of the appliance 60. As a result, mandibular growth progresses in a forward direction. The lingual tabs 66 may also assist in the correction of overjet. A hinged area 70 may also be provided which may connect the upper portion 68 of the dental appliance to a lower portion 72. The dental appliance 60 illustrated in FIGS. 4A and 4B may be worn to treat the dental conditions of users of various ages having various numbers, sizes and shapes of teeth with minimal or no adjustments or appointments. In an embodiment, the dental appliance 60 may have slots for various numbers of teeth.

Figure 5:
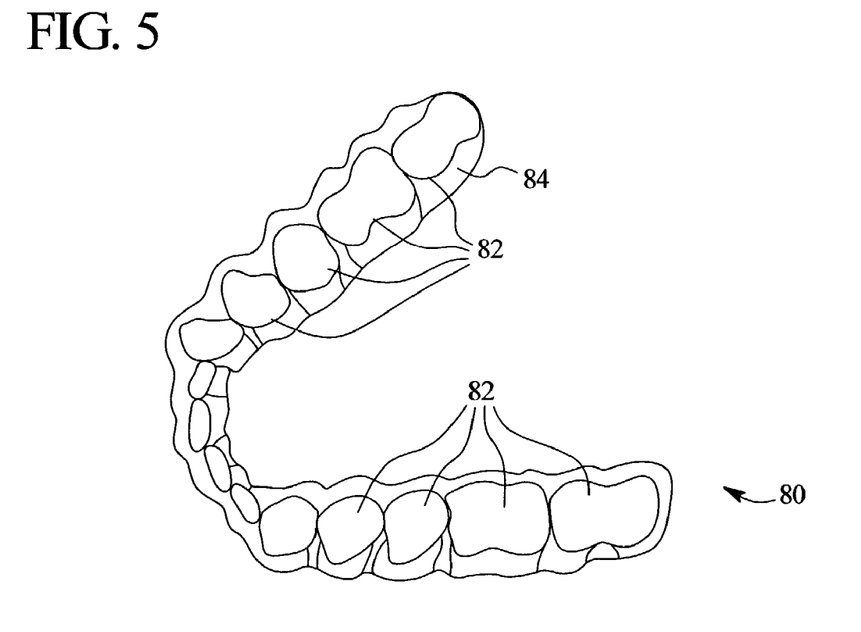
FIG. 5 illustrates a top plan view of a dental appliance in another embodiment of the present invention.

A dental appliance 80 is illustrated in FIG. 5 wherein the dental appliance 80 has sockets 82 for receiving teeth of the user. The sockets 82 may be shaped to correspond to a shape of an individual tooth of the user. In an alternative, the sockets 82 may be flat. In an embodiment, the dental appliance 80 may have any combination of sockets 82 sized for one or more teeth wherein the sockets 82 are shaped to correspond with a shape of the teeth and/or are flat. In addition, the dental appliance 80 may have a shell 84 surrounding the sockets 82 and/or part of the gums of the user. The shell 84 may be constructed, for example, from plastic or like material. The dental appliance 80 may be formed by suction of a heated sheet of plastic onto a model of the teeth of the user. The suction may be provided by a vacuum. Alternatively, the heated sheet may be pressed over the teeth of a model of the user by pressure. An apparatus supplied by DENTAURAM of Germany, for example, may be used to press the heated sheet over the model of the user. In another embodiment, the dental appliance 80 may be formed by stereolithography from a three-dimensional digital image representation of a model. The shell 84 may be placed around the teeth of the user when the dental appliance 80 is worn. The shell 84 may then secure the dental appliance 80 to the teeth of the user. The dental appliance 80 illustrated in FIG. 5 may preferably be designed from a computer-generated three-dimensional digital model. The model may be created after obtaining an impression and/or image of the teeth of the user. The dental appliance 80 may be constructed separately as an upper portion and a lower portion wherein the upper portion and the lower portion may be attached, for example, by snaps, hook and loop fasteners, or the like or may be attached in a permanent manner as a single unit. In an embodiment, the upper portion and the lower portion may be connected by a hinge (not shown) which may assist in movement of the upper portion toward or away from the lower portion. In an alternative embodiment, the hinge may provide resistance against movement of the upper portion toward or away from the lower portion.

Figure 6:
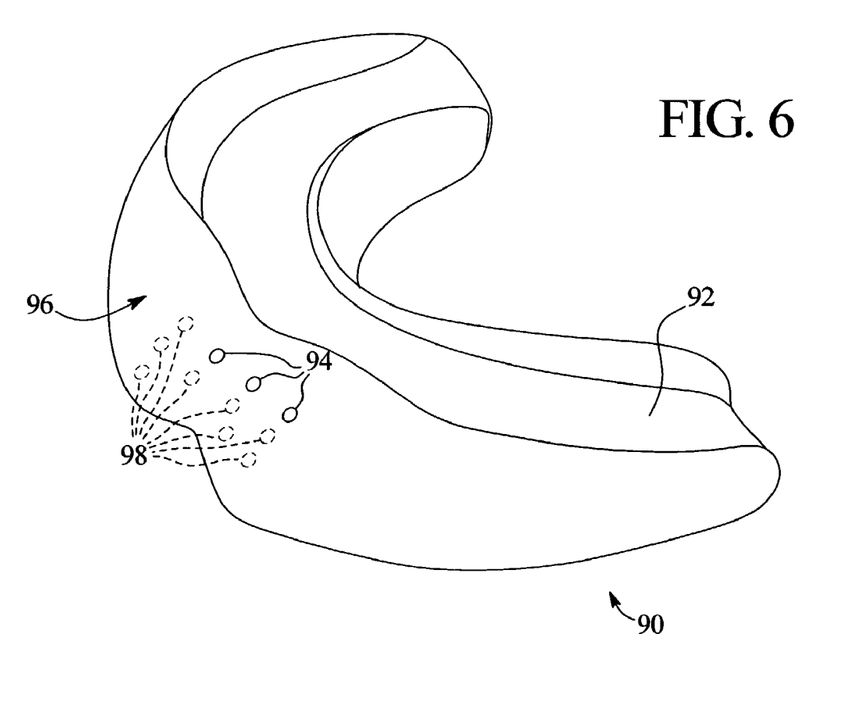
FIG. 6 illustrates a perspective view of a dental appliance in an embodiment of the present invention.

FIG. 6 illustrates a dental appliance 90 which may have a flat area 92 as an occlusal surface. The dental appliance 90 may be constructed of rubber, plastic, or the like. Holes 94, or similarly-shaped openings may be provided at a front end 96 of the dental appliance 90 to facilitate breathing through the dental appliance 90 by the patient while wearing the dental appliance 90 within the mouth. In other embodiments, the dental appliance 90 may have sockets for each of the individual teeth or may have sockets for only some of the teeth of the user. A remainder of the dental appliance may have flat areas, or slots, or may have a single flat area without sockets. Protrusions 98 may be provided to indicate to the user to reduce activity of the lip. The dental appliance 90 may be designed to treat the dental conditions of users of any age.

Figure 7:
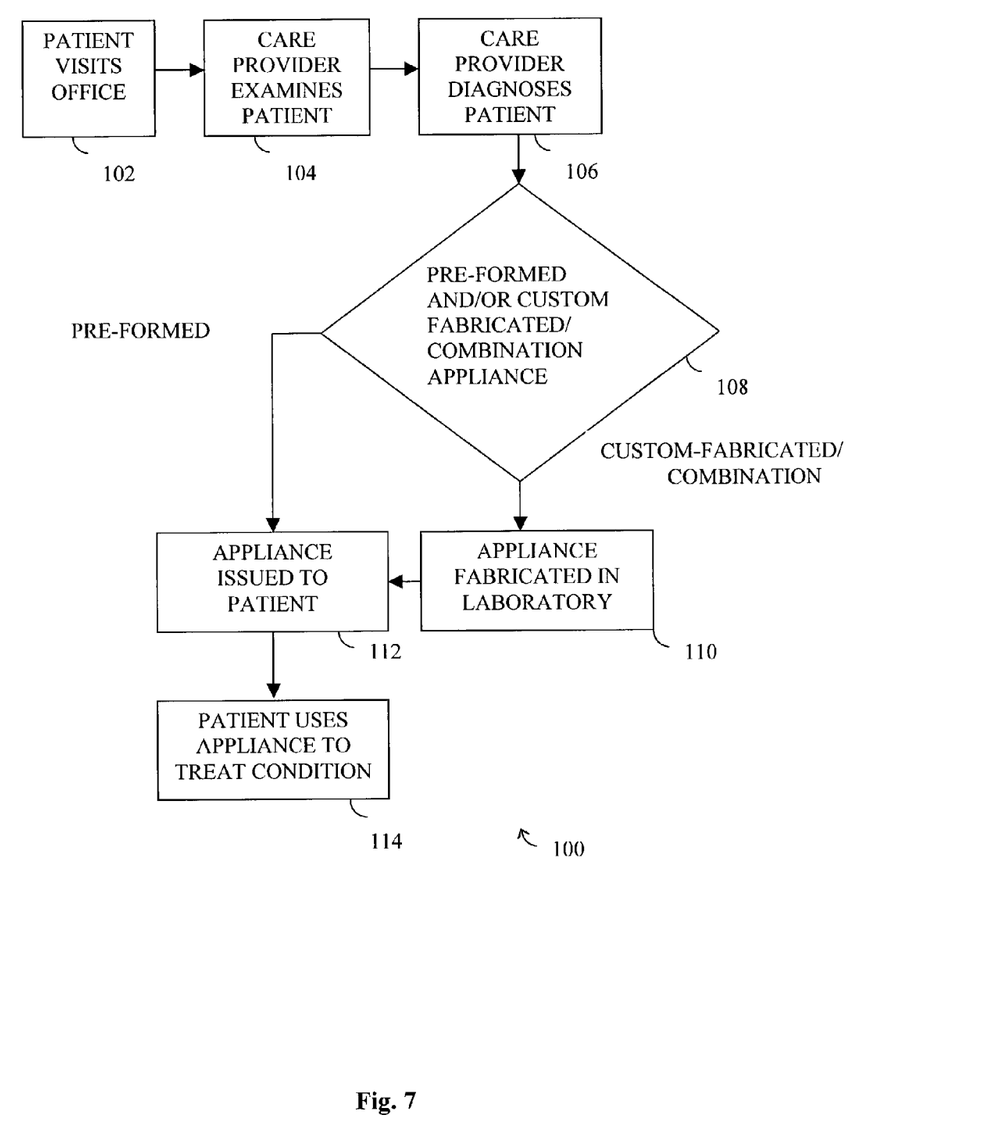
FIG. 7 illustrates a flow chart of a method for distributing a dental appliance in an embodiment of the present invention.

Referring now to FIGS. 7 through 12, various methods are provided for distributing the dental appliances described above. Specifically, FIG. 7 illustrates a method 100 for distributing dental appliances to a prospective patient. The method 100 may have a first step 102 wherein the patient visits an office of a dental care provider, such as, for example, a dentist, orthodontist, or the like. The care provider may be the owner of the office. The care provider may examine the patient, as shown at step 104. Based on the examination, the care provider may diagnose the patient as having a dental condition, as shown at step 106. The care provider may then choose a pre-formed, or customized (fabricated), or combination pre-formed and customized dental appliance to treat the dental condition of the patient, as shown at step 108. In another embodiment, the dental appliance may be partially pre-formed and partially customized. If the care provider decides that a fabricated appliance may be used to treat the patient, the appliance may be fabricated at a laboratory, as shown at step 110. However, if the dental appliance to be administered to the patient is pre-formed, the care provider may store the pre-formed dental appliance at the office. The care provider may then issue the dental appliance to the patient, as shown at step 112. In an embodiment, oral and/or written instructions may be provided with the dental appliance. The patient may wear and/or may apply the dental appliance to treat the condition, as shown at step 114. In an embodiment, more than one dental appliance may be provided to treat various stages of a dental condition. As a result, the patient may require few, if any, adjustments to the appliance and/or few, if any, subsequent visits with the care provider to receive treatment for the dental condition.

Figure 8:
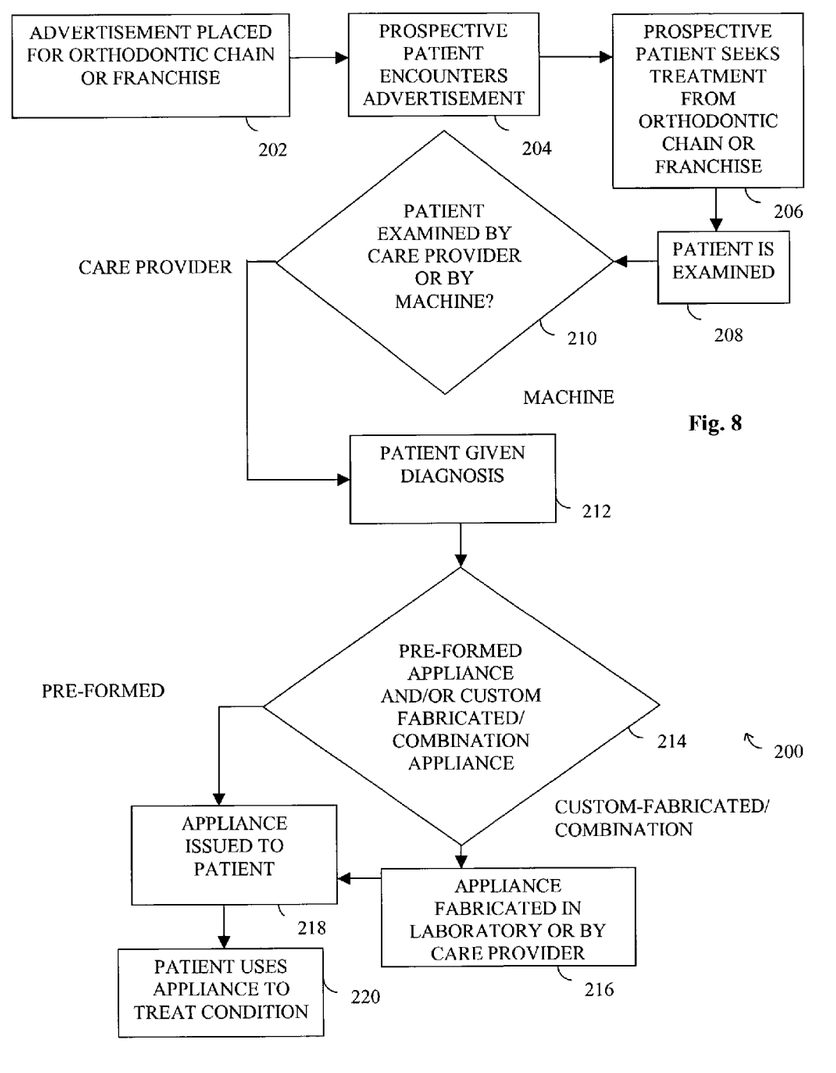
FIG. 8 illustrates a flow chart of a method for distributing a dental appliance in another embodiment of the present invention.

FIG. 8 illustrates another method 200 for distributing dental appliances to prospective patients through an orthodontic chain of offices or franchised offices. The office may be managed by, for example, the owner of the orthodontic chain. The owner may be, for example, a stockholder of a corporation associated with the orthodontic chain. Alternatively, the owner may be a franchisee. In another embodiment, the office may be managed by salaried employees and/or independent contractors. The employees or the independent contractors may be provided with commissions based on services rendered or may be compensated by salary. The chain of offices may have set fees for various services, such as, for example, fluoride treatments, whitening treatments, or other preventative procedures.

In a first step, shown at step 202, an advertisement may be placed for products and/or services provided by the orthodontic chain. The advertisement may be presented via television, radio, internet, direct mail, or other method. The prospective patient may encounter the advertisement, as shown at step 204. The patient may then seek treatment from one of the offices of the orthodontic chain or franchise, as shown at step 206. The patient may be examined, as shown at step 208. Specifically, the patient may be examined by a representative of the orthodontic chain, such as a dentist, orthodontist, or the like, as shown at step 210; alternatively, the patient may be examined by a machine which may take images of the patient, such as x-ray images, magnetic resonance images, catscan, photos, or the like. Impressions of the patient may also be taken. The patient may then be diagnosed as having a dental condition requiring a dental appliance or appliances, as shown at step 212. The dental appliance(s) may be any of those described above.

The care provider at the office may determine whether the patient requires a pre-formed appliance or a customized, fabricated appliance, as shown at step 214. In one embodiment, the dental appliance may be partially preformed and partially customized. If the dental appliance is to be fabricated, the dental appliance may be fabricated at a laboratory or by the care provider, as shown at step 216. If the required dental appliance is pre-formed, the office may already store the dental appliance. The dental appliance may then be issued to the patient, as shown at step 218. The patient may then use the dental appliance to treat the dental condition, as shown at step 220. If more than one dental appliance is issued, the patient may wear a different dental appliance for each stage of treatment. As a result, the patient may require few, if any, subsequent adjustments and/or visits to the orthodontic chain to treat the dental condition.

Figure 9:
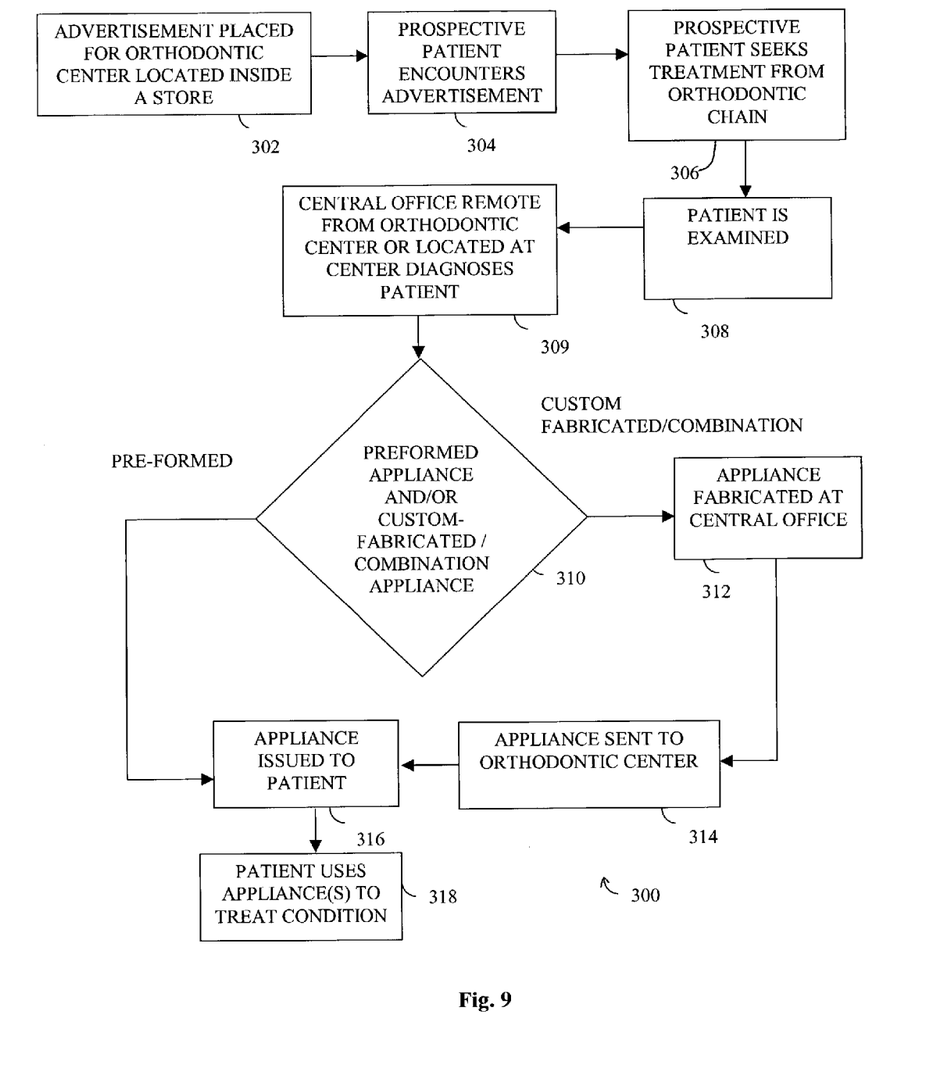
FIG. 9 illustrates a flow chart of a method for distributing a dental appliance in another embodiment of the present invention.

In another method 300, illustrated in FIG. 9, dental appliances are distributed to prospective patients by an orthodontic center located within a store or mass merchandising outlet or mart. The orthodontic center may be located, for example, within a shopping center, a shopping mall, or the like. An advertisement may be placed for the products and/or services provided by the orthodontic center, as shown at step 302. The advertisements may be placed via television, radio, internet, direct mail, billboard, or the like. The prospective patient may encounter the advertisement, as shown at step 304. The prospective patient may then seek treatment from the orthodontic center, as shown at step 306. The patient may be examined by a care provider representing the orthodontic center or by a machine or set of machines located at the center, as shown at step 308. The care provider may be, for example, a dental professional, hygienist, trained assistant, x-ray technician, or the like. The examination may require digital images and/or x-rays of the patient, or the like. The examination results may be analyzed by a central office located remote from the orthodontic center. In an embodiment, the examination results may be examined at the orthodontic center. The central office may have care providers who may diagnose the patient.

The results may be transferred to the central office via facsimile, modem, direct mail, or other method. The central office may then diagnose the patient, as shown at step 309. The central office may also determine whether the patient requires a pre-formed, fabricated, or combination dental appliance as shown at step 310. If the appliance is to be fabricated, the appliance may be fabricated at the central office and/or other location, as shown at step 312. The appliance may then be delivered to the orthodontic center, as shown at step 314. If the required dental appliance is pre-formed, the orthodontic center may already store the dental appliance. In an embodiment, the dental appliance may be partially pre-formed and partially custom-fabricated. The dental appliance may then be issued to the patient, as shown at step 316. The dental appliance may be accompanied by oral and/or written instructions. In an embodiment, the instructions may be customized for the patient and/or provided by the care providers at the central office. The patient may then use the dental appliance to treat the dental condition, as shown at step 318. As a result, the patient may require few, if any, subsequent adjustments and/or subsequent visits to the orthodontic center to treat the dental condition.

Figure 10:
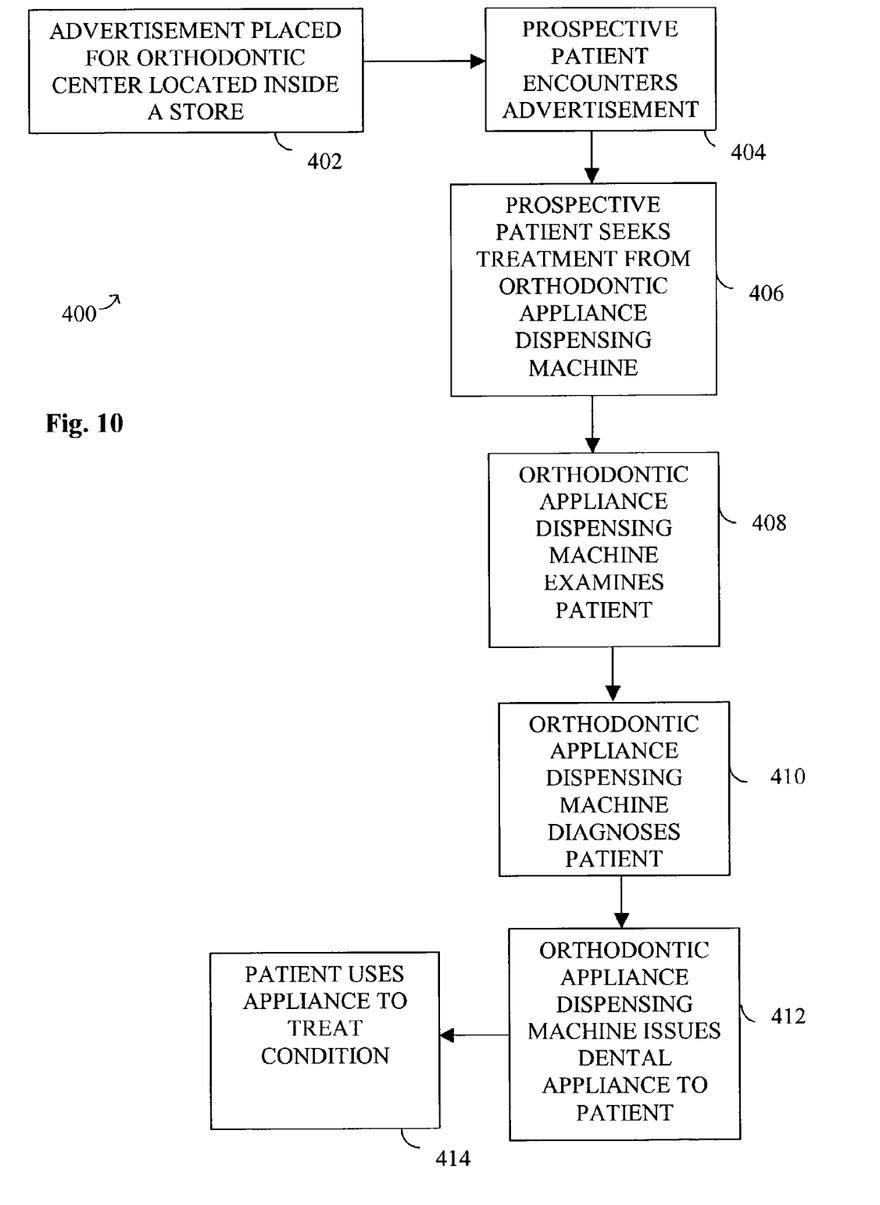
FIG. 10 illustrates a flow chart of a method for distributing a dental appliance in another embodiment of the present invention.

Referring now to FIG. 10, a method 400 is provided for distributing dental appliances to prospective patients through a dental appliance dispensing machine which may be located within a store, shopping center, or hospital clinic, or the like. In a first step 402 of the method 400, an advertisement may be placed for the dental appliance dispensing machine. The advertisement may be provided via methods similar to those described above. The prospective patient may encounter the advertisement, as shown at step 404. The patient may then seek treatment from the dental appliance dispensing machine, as shown at step 406. The machine may examine the patient, as shown at step 408, by taking images of any sort and/or impressions of the mouth of the patient. The machine may be connected to a processor which may provide a diagnosis for the patient based on the images and/or impressions taken, as shown at step 410. In another embodiment, the images and/or impressions may be examined remotely by a computer program or by a care provider. The care provider and/or computer may then provide the diagnosis.

The dental appliance dispensing machine may then issue a dental appliance, similar to those described above, to the patient to treat a dental condition of the patient, as shown at step 412. Several types of dental appliances may be provided by the dental appliance dispensing machine, including, but not limited to, dental appliances for patients of varying age or conditions; dental appliances having varied sizes; and dental appliances having a single size which may treat patients having various-sized mouths. Preferably, the dental appliance is pre-formed. In other embodiments, the dental appliance may be partially preformed and partially customized, or may be fully customized. In an embodiment, more than one dental appliance may be issued to the patient to address different stages of treatment of a dental condition. The dental appliance may be dispensed upon payment by, for example, a credit card, debit card, or the like. The patient may then use the appliance to treat the dental condition, as shown at step 414. As a result, the patient may not require subsequent visits to the dental appliance dispensing machine or to a dental provider for treatment of the dental condition.

Figure 11:
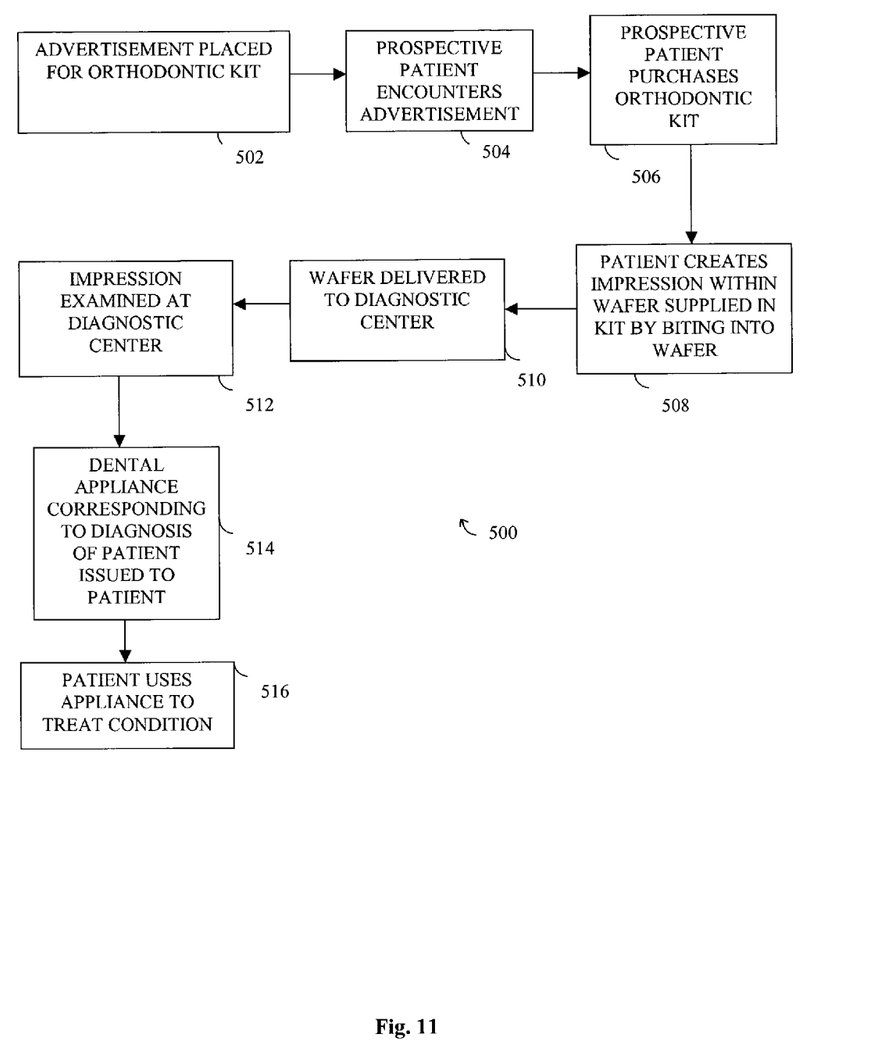
FIG. 11 illustrates a flow chart of a method for distributing a dental appliance in another embodiment of the present invention.

FIG. 11 illustrates a method 500 for distributing dental appliances to prospective patients by orthodontic kits which may be sold in stores. The store may be a pharmacy, retailer, or the like. The kit may have items, such as, for example, a dental appliance, fluoride gel, paste, whitening material, or the like. In an embodiment, a plastic or wax wafer, for example, may be provided within the kit which the patient may use to create an impression by biting into the wafer. Moreover, any apparatus suitable for obtaining an impression of the user may be implemented within the orthodontic kit. The dental appliance may be of a type which is sized and/or shaped to fit within the mouth of various users, such as that illustrated in FIGS. 1, 2A, 2B, 3, 4A, 4B, 5 and 6. A packaging of the kit may have representative and contraindicated cases for review by the patient prior to purchase of the kit.

An advertisement for the orthodontic kit may be placed via television, radio, internet, direct mail, or the like, as shown at step 502. A prospective patient may encounter the advertisement, as shown at step 504. The patient may then purchase the orthodontic kit, as shown at step 506. Next, the patient may remove the wafer within the orthodontic kit and make an impression within the wafer by biting into the wafer, as shown at step 508. The wafer may be delivered from the store to a diagnostic center, as shown at step 510. The wafer may then be examined at the diagnostic center, as shown at step 512.

A dental appliance may then be chosen and/or created for the patient and issued to the patient upon payment of a fee, as shown at step 514. A phone number may be provided for a support service which the patient may use to answer questions concerning use of the dental appliance. The patient may use the dental appliance to treat a dental condition, as shown at step 516. As a result, the patient may require few, if any, adjustments and/or visits to a dental care provider, for example, for treatment of the dental condition.

Figure 12:
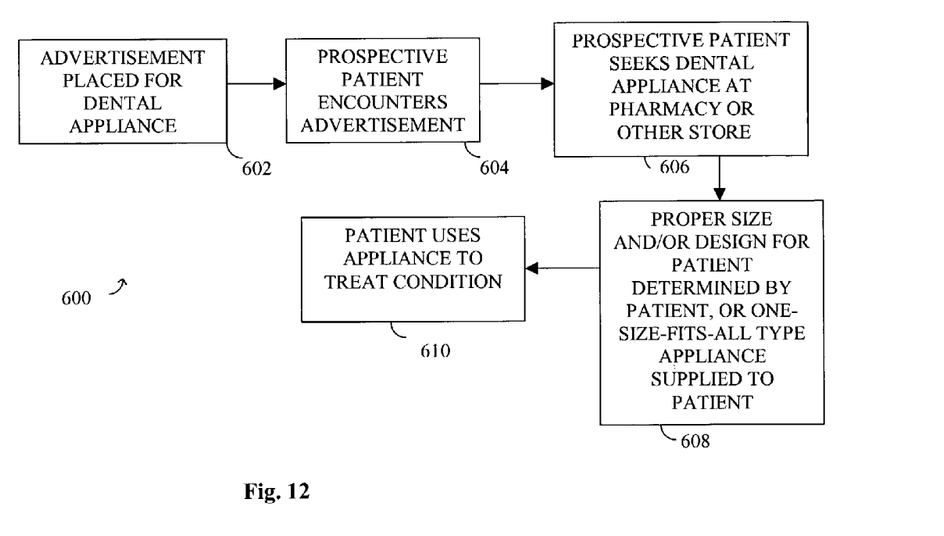
FIG. 12 illustrates a flow chart of a method for distributing a dental appliance in another embodiment of the present invention.

Referring now to FIG. 12, a method 600 is provided for distributing a dental appliance to a prospective patient in an over-the-counter manner. The dental appliance may be any type as described above. An advertisement for the dental appliance may be placed via television, radio, internet, direct mail, or the like, as shown at step 602. The prospective patient may encounter the advertisement, as shown at step 604. The prospective patient may then visit a store which offers the dental appliance for sale, as shown at step 606. The dental appliance may be available in one or more sizes. Consequently, the patient may review a packaging of the dental appliance to determine the proper type and/or size of dental appliance that the patient requires, as shown at step 608. In an embodiment, the dental appliance may be sized to fit within a mouth of any size. The packaging may have, for example, an image of a tooth or teeth with which the patient can compare his or her own teeth. The packaging may have additional information such as, for example, information regarding appropriate and inappropriate examples of a dental condition. The information may assist the patient in determining an appropriate dental appliance. After the proper type and/or size of appliance is determined, the patient may use the dental appliance to treat the dental condition, as shown at step 610.

It should be understood that various changes and modifications to the presently preferred embodiments described herein will be apparent to those skilled in the art. Such changes and modifications may be made without departing from the spirit and scope of the present invention and without diminishing its attendant advantages.

I claim:

1. A method for distributing a dental appliance to a patient, the method comprising the steps of:
    manufacturing a plurality of types of pre-formed dental appliances before diagnosing the patient wherein each type of preformed dental appliance corresponds to one of a plurality of types of orthodontic conditions;
    obtaining an image of an interior of a mouth of the patient using an image capturing device wherein the image is obtained by the image capturing device after the plurality of types of pre-formed dental appliances are manufactured;
    diagnosing the patient based on the image of the interior of the mouth of the patient wherein the patient is diagnosed after the plurality of types, of pre-formed dental appliances are manufactured;
    determining if the patient is treatable by one of the plurality of types of pre-formed dental appliances; and
    providing the patient with the dental appliance wherein the dental appliance is one of the types of pre-formed dental appliance corresponding to the type of orthodontic condition diagnosed in the patient if the patient is, treatable by one of the plurality of types of pre-formed dental appliances wherein the dental appliance is a customized dental appliance if the patient is not treatable by one of the types of pre-formed dental appliances.

2. The method of claim 1 wherein the patient is provided with the dental appliance by a dispensing apparatus that stores the dental appliance.

3. The method of claim 1 wherein the patient is provided with the dental appliance by a dispensing apparatus that stores the dental appliance and further wherein the image capturing device is connected to the dispensing apparatus.

4. The method of claim 1 wherein the pre-formed dental appliance is delivered to the patient from a location remote from the office.

5. The method of claim 1 further comprising the step of:
    customizing the pre-formed dental appliance prior to receipt of the dental appliance by the patient.

6. A method for distributing a dental appliance to a patient through an office within a chain of offices providing dental care, the method comprising the steps of:
    manufacturing a plurality of pre-formed dental appliances;
    obtaining an image of an interior of a mouth of the patient using an image capturing device wherein the image is obtained by the image capturing device after the plurality of pre-formed dental appliances are manufactured;
    diagnosing the patient based on the image off the interior of the mouth of the patient wherein the patient is diagnosed after the plurality of pre-formed dental appliances are manufactured;
    determining if the patient is treatable by one of the plurality of pre-formed dental appliances; and
    providing the patient with a plurality of dental appliances wherein each of the plurality of dental appliances is the type of dental appliance corresponding to the type of orthodontic condition diagnosed in the patient and further wherein each of the plurality of dental appliances is worn consecutively without further examination of the patient wherein the plurality of dental appliances are the pre-formed dental appliances if the patient is treatable by the pre-formed dental appliances wherein the plurality of dental appliances are customized dental appliances if the patient is not treatable by the pre-formed dental appliances.

7. The method of claim 6 wherein the patient is diagnosed at the office and the plurality of dental appliances are provided at a location remote from the office.

8. The method of claim 6 wherein the patient is diagnosed at the office and the image of the mouth is obtained by the image capturing device at a location remote from the office.

9. The method of claim 6 wherein the plurality of dental appliances is provided by a machine connected to the image capturing device.

10. The method of claim 6 wherein the image is obtained by a care provider.

11. The method of claim 6 wherein each of the plurality of dental appliances is manufactured at a location remote from the office.

12. The method of claim 6 wherein the image is obtained at a location remote from the office.

13. A method for distributing a dental appliance to a patient through an orthodontic center located within a shopping center, the method comprising the steps of:
    manufacturing a plurality of types of pre-formed dental appliances before examining the patient wherein each type of pre-formed dental appliance corresponds to one of a plurality of types of orthodontic conditions;
    examining the patient at the orthodontic center wherein the patient creates an impression in a wafer by biting into the wafer and further wherein the patient is examined after the plurality of types of pre-formed dental appliances are manufactured;
    transmitting the wafer from the orthodontic center to a central office wherein the central office is remote from the orthodontic center and further wherein the wafer is transmitted after the plurality of types of pre-formed dental appliances are manufactured;
    diagnosing the patient as having one of the types of orthodontic conditions wherein the central office diagnoses the patient based on the impression in the wafer transmitted from the orthodontic center; and
    providing the patient with the type of dental appliance corresponding to the type of orthodontic condition diagnosed in the patient.

14. The method of claim 13 further comprising the step of:
    customizing the dental appliance prior to providing the patient with the dental appliance.

15. The method of claim 13 further comprising the step of:
    providing the dental appliance to the patient at a third location wherein the third location is remote from the orthodontic center and the central office.

16. The method of claim 13 further comprising the step of:
    delivering the dental appliance to the orthodontic center prior to providing the dental appliance to the patient.

17. The method of claim 13 wherein the patient is examined by a machine.

18. The method of claim 13 further comprising the step of:
    treating a malocclusion with the dental appliance, 19. The method of claim 13 wherein the patient is provided with the dental appliance at the orthodontic center.

20. A method for distributing a dental appliance to a patient, the method comprising the steps of:
    manufacturing one or more types of pre-formed dental appliances which correspond to one or more types of orthodontic conditions wherein the one or more types of pre-formed dental appliances are manufactured before diagnosing the patient;

placing a dental appliance dispensing apparatus in a venue of a common carrier wherein the dental appliance dispensing apparatus stores the one or more types of pre-formed dental appliances which correspond to one or more types of orthodontic conditions;

obtaining an image of an interior of a mouth of the patient wherein the image of the interior of the mouth of the patient is obtained after the one or more types of pre-formed dental appliances are manufactured;

diagnosing the patient as having one of the types of orthodontic conditions based on the image of the interior of the mouth of the patient wherein the image of the interior of the mouth of the patient is obtained after the one or more types of dental appliances are manufactured;

determining if the patient is treatable by one of the plurality of types of pre-formed dental appliances;

dispensing the dental appliance from the dental appliance dispensing apparatus to the patient wherein the dental appliance is one of the plurality of types of pre-formed appliances if the patient is treatable by one of the plurality of types of pre-formed appliances wherein the dental appliance is a customized dental appliance if the patient is not treatable by one of the plurality of types of pre-formed appliances.

21. The method of claim 20 further comprising the step of: treating a malocclusion with the dental appliance.

22. The method of claim 20 wherein the image is obtained at the dental appliance dispensing apparatus.

23. The method of claim 20 further comprising the step of: obtaining an impression of the interior of the mouth of the patient using a wafer provided by the dental appliance dispensing apparatus wherein the impression is used to generate the image of the interior of the mouth of the patient.

24. A system for distributing a dental appliance to a patient, the system comprising:
a dental appliance dispensing apparatus having an image capturing device for obtaining an image of an interior of a mouth of the patient;
a plurality of types of dental appliances stored within the dental appliance dispensing apparatus wherein each type of the plurality of types of dental appliances correspond to a type of orthodontic condition wherein the plurality of types of dental appliances are manufactured before the image is obtained by the dental appliance dispensing apparatus; and
a central processing unit located remote from the dental appliance dispensing apparatus wherein the central processing unit is connected to the dental appliance dispensing apparatus and further wherein the central processing unit diagnoses the image obtained of the mouth of the patient into one of the types of orthodontic conditions wherein the central processing unit directs the dental appliance dispensing apparatus to dispense one of the plurality of types of dental appliances to the patient.

25. The system of claim 24 wherein two or more of the dental appliances correspond to consecutive stages of treatment of a malocclusion.

26. A method for distributing a dental appliance to a patient wherein the dental appliance is one of a plurality of types of pre-formed dental appliances wherein each type of pre-formed dental appliance corresponds to one of a plurality of types of orthodontic conditions, the method comprising the steps of:
designing the plurality of types of pre-formed dental appliances before diagnosis of the patient;

providing an orthodontic kit wherein the orthodontic kit contains a wafer and further wherein the wafer obtains an impression of teeth wherein the orthodontic kit is provided after the plurality of types of pre-formed dental appliances are designed;

diagnosing one of the orthodontic conditions based on the impression wherein diagnosis is performed after the plurality of types of pre-formed dental appliances are designed; and selecting the pre-formed dental appliance based on the impression of teeth obtained by the wafer.

27. The method of claim 26 further comprising the step of: delivering one of the types of dental appliances to a location where the impression of the wafer was obtained.

28. The method of claim 26 further comprising the step of: delivering one of the types of dental appliances to the patient based on the type of orthodontic condition diagnosed.

29. The method of claim 26 further comprising the step of: customizing the pre-formed dental appliance prior to delivering the dental appliance.

30. The method of claim 26 wherein diagnosis occurs at a location remote from the patient.

31. The method of claim 26 wherein the orthodontic kit contains information regarding at least one type of the orthodontic conditions.

32. A method for distributing a dental appliance to a patient through a venue wherein the dental appliance is one of a plurality of types of dental appliances wherein each type of dental appliance corresponds to one of a plurality of types of orthodontic conditions, the method comprising the steps of:
manufacturing the plurality of types of dental appliances before diagnosis of the patient;
obtaining an image of an interior of a mouth of the patient wherein the image is obtained at the venue using an image capturing device and further wherein the image is obtained by the image capturing device after the plurality of types of dental appliances are manufactured;
transmitting the image to a location remote from the venue;
diagnosing the patient as having one of the types of orthodontic conditions based on the image of the interior of the mouth of the patient wherein the patient is diagnosed at the location remote from the venue and further wherein the patient is diagnosed after the plurality of types of dental appliances are manufactured;
determining if the patient is treatable by one of the plurality of types of pre-formed dental appliances; and
providing the patient with the dental appliance wherein the dental appliance is one of the plurality of types of pre-formed dental appliances if the patient is treatable by one of the plurality of types of pre-formed dental appliances and further wherein the dental appliance is a customized appliance if the patient is not treatable by one of the plurality of types of pre-formed dental appliances wherein the patient requires no subsequent interaction with an individual associated with the venue after the patient receives the dental appliance to treat the orthodontic condition of the patient and further wherein the type of dental appliance corresponding to the type of orthodontic condition diagnosed in the patient is provided at the venue.

33. The method of claim 32 wherein the venue is an office of a care provider.

34. The method of claim 32 wherein the venue is an office in a chain of offices.

35. The method of claim 32 wherein the venue is an orthodontic center within a shopping center.

36. The method of claim 32 wherein the venue is a dental appliance dispensing apparatus at a location of a common carrier wherein the image capturing device is connected to the dental appliance dispensing apparatus.

37. A method for distributing a dental appliance to a patient through a venue wherein the dental appliance is one of a plurality of types of dental appliances wherein each type of dental appliance corresponds to one of a plurality of types of orthodontic conditions, the method comprising the steps of:
manufacturing the dental appliance before diagnosing the patient;
obtaining an image of an interior of a mouth of the patient wherein the image is obtained by the patient creating an impression in a wafer wherein the image is obtained after the dental appliance is manufactured;
sending the wafer to a diagnostic center;
diagnosing the patient as having one of the types of orthodontic conditions based on the image of the interior of the mouth of the patient wherein the patient is diagnosed at the diagnostic center after the dental appliance is manufactured; and
providing the patient with the type of dental appliance corresponding to the type of orthodontic condition diagnosed in the patient wherein the patient wherein the dental appliance is provided to the patient at the venue wherein the venue is located at a location remote from the diagnostic center.

38. The method of claim 37 wherein the wafer is provided at the venue.

39. The method of claim 37 wherein the wafer is provided in a kit purchased at a store.

40. The method of claim 37 wherein the venue is an orthodontic center within a shopping center.

41. The method of claim 37 wherein the venue is a dental appliance dispensing apparatus at a location of a common carrier.

42. A method for providing a dental appliance to a patient, the method comprising the steps of:
manufacturing the dental appliance before diagnosing the patient;
providing the patient with a wafer sized to be placed within a mouth of the patient wherein the wafer is provided at a first location after the dental appliance is manufactured;
taking an impression of the mouth of the patient wherein the impression is obtained by the patient biting the wafer;
sending the wafer to a second location;
diagnosing the patient with an orthodontic condition associated with teeth of the patient wherein the patient is diagnosed at the second location after the dental appliance is manufactured; and
providing a venue accessible by the patient to obtain the dental appliance to correct the orthodontic condition diagnosed in the patient wherein the venue is selected from a group consisting of an office of a care provider, an office in a chain of offices, an orthodontic center within a shopping center, and a dental appliance dispensing apparatus wherein the first location, the second location and the venue are different locations.

43. The method of claim 42 wherein the dental appliance is one of a plurality of types of dental appliances wherein each type of dental appliance corresponds to one of a plurality of types of orthodontic conditions.

44. The method of claim 42 wherein the patient does not require subsequent interaction with the venue after receiving the dental appliance.

45. The method of claim 42 wherein the patient requires one subsequent interaction with the venue after receiving the dental appliance.

46. The method of claim 42 wherein the venue is remote from the patient.

47. The method of claim 42 wherein the step of diagnosing the patient occurs at a location remote from the venue.

48. A method for distributing a dental appliance to a patient through a venue wherein the dental appliance is sized to fit users of various sizes of dentitions wherein the dental appliance corresponds to one of a plurality of types of orthodontic conditions, the method comprising the steps of:
manufacturing the dental appliance before diagnosing the patient;
obtaining an image of a dentition of the patient using an image capturing device wherein the image is obtained by the image capturing device after the dental appliance is manufactured;
determining a size of the dentition of the patient wherein the size of the dentition of the patient is determined from the image of the dentition;
diagnosing the patient as having one of the types of orthodontic conditions wherein the type of orthodontic condition is determined from the image of the dentition wherein the patient is diagnosed after the dental appliance is manufactured; and
providing the patient with the dental appliance corresponding to the type of orthodontic condition diagnosed in the patient and sized to correspond to the size of the dentition of the patient wherein the patient requires no subsequent interaction with an individual associated with the venue after the patient receives the dental appliance to treat the orthodontic condition of the patient.

49. The method of claim 48 wherein the venue is an office of a care provider.

50. The method of claim 48 wherein the venue is an office in a chain of offices.

51. The method of claim 48 wherein the venue is an orthodontic center within a shopping center.

* * * * *